(12) United States Patent
Sarrafzadeh et al.

(10) Patent No.: US 11,450,413 B2
(45) Date of Patent: Sep. 20, 2022

(54) SYSTEMS AND METHODS FOR MISSING DATA IMPUTATION

(75) Inventors: Majid Sarrafzadeh, Anaheim Hills, CA (US); Myung-Kyung Suh, Albuquerque, NM (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 950 days.

(21) Appl. No.: 14/241,431

(22) PCT Filed: Aug. 27, 2012

(86) PCT No.: PCT/US2012/052544
§ 371 (c)(1),
(2), (4) Date: Feb. 26, 2014

(87) PCT Pub. No.: WO2013/033028
PCT Pub. Date: Mar. 7, 2013

(65) Prior Publication Data
US 2014/0207493 A1 Jul. 24, 2014

Related U.S. Application Data

(60) Provisional application No. 61/528,065, filed on Aug. 26, 2011.

(51) Int. Cl.
*G16H 10/60* (2018.01)
*G16H 50/20* (2018.01)
(Continued)

(52) U.S. Cl.
CPC ........... *G16H 10/60* (2018.01); *A61B 5/7264* (2013.01); *G06N 7/005* (2013.01); *G16H 40/67* (2018.01); *G16H 50/20* (2018.01); *A61B 5/7267* (2013.01)

(58) Field of Classification Search
CPC .... A61B 5/00; A61B 5/05; G06E 1/00; G06F 15/18; G06Q 10/04; G06Q 10/10
(Continued)

(56) References Cited

U.S. PATENT DOCUMENTS 6,810,368 B1 10/2004 Pednault
7,467,119 B2* 12/2008 Saidi ................... G06F 19/3443
600/407

(Continued)

OTHER PUBLICATIONS

Bayesian Network Representation, Lecture 2—Mar. 30, 2011, CSE 515, Statistical Methods, Spring 2011, Instructor: Su-In Lee University of Washington, Seattle.*

(Continued)

*Primary Examiner* — Dilek B Cobanoglu
(74) *Attorney, Agent, or Firm* — Foley & Lardner LLP (57) ABSTRACT

Congestive heart failure (CHF) is a leading cause of death in the United States. WANDA is a wireless health project that leverages sensor technology and wireless communication to monitor the health status of patients with CHF. The first pilot study of WANDA showed the system's effectiveness for patients with CHF. However, WANDA experienced a considerable amount of missing data due to system misuse, nonuse, and failure. Missing data is highly undesirable as automated alarms may fail to notify healthcare professionals of potentially dangerous patient conditions. Embodiments of the present disclosure may utilize machine learning techniques including projection adjustment by contribution estimation regression (PACE), Bayesian methods, and voting feature interval (VFI) algorithms to predict both non-binomial and binomial data. The experimental results show that the aforementioned algorithms are superior to other methods with high accuracy and recall.

21 Claims, 6 Drawing Sheets

(51) Int. Cl.
 *A61B 5/00* (2006.01)
 *G06N 7/00* (2006.01)
 *G16H 40/67* (2018.01)

(58) Field of Classification Search
 USPC ........ 600/300, 301, 407; 706/21, 12; 703/22
 See application file for complete search history.

(56) References Cited

U.S. PATENT DOCUMENTS

| | | | |
|---|---|---|---|
| 7,730,003 B2* | 6/2010 | Pinto | G06Q 10/04 |
| | | | 703/22 |
| 7,912,528 B2* | 3/2011 | Krishnan | G06F 19/345 |
| | | | 382/128 |
| 9,734,290 B2* | 8/2017 | Srinivas | G06Q 10/10 |
| 2006/0184475 A1 | 8/2006 | Krishnan | |
| 2008/0133275 A1 | 6/2008 | Haug | |
| 2009/0076342 A1* | 3/2009 | Amurthur | A61B 5/0002 |
| | | | 600/301 |
| 2010/0057651 A1 | 3/2010 | Fung et al. | |
| 2011/0105852 A1* | 5/2011 | Morris | G06Q 10/10 |
| | | | 600/300 |
| 2011/0202486 A1* | 8/2011 | Fung | G06N 7/005 |
| | | | 706/12 |

OTHER PUBLICATIONS

A New Approach to Fitting Linear Models in High Dimensional Spaces, Yong Wang, University of Waikato, Nov. 2000.*

Google search, May 1, 2017.*
ip.com search, May 5, 2022 (Year: 2022).*
Demiroz G et al. (1997), "Classification by Voting Feature Intervals" In: "Correct System Design", Jan. 1, 1997, Springer International Publishing, Cham 032548, vol. 1224, pp. 85-92.
Extended European Search Report for European Patent Application No. 12828066.6 dated Jun. 7, 2016.
Suh M-K et al. (2010), "An Automated Vital Sign Monitoring System for Congestive Heart Failure Patients", Proceedings of the 1st ACM International Health Informatics Symposium, 2010, pp. 108-117.
Suh M-K et al. (2010), "Wanda B.: Weight and activity with blood pressure monitoring system for heart failure patients", World of Wireless Mobile and Multimedia Networks (WOWMOM), 2010 IEEE International Symposium on A, IEEE, Piscataway, NJ, USA, Jun. 14, 2010, pp. 1-6.
Suh M-K et al. (2011), "A Remote Patient Monitoring System for Congestive Heart Failure", J Med Syst. 2011, 35(5):1165-1179.
Suh M-K et al. (2011), "Missing data imputation for remote CHF patient monitoring systems", Engineering in Medicine and Biology Society, EMBC, 2011 Annual International Conference of the IEEE, IEEE, Aug. 20, 2011, pp. 3184-3187.
Wang Y et al. (2002), "Modeling for optimal probability prediction", Proceedings of ICML, Jan. 1, 2002.
International Search Report and Written Opinion dated Jan. 31, 2013, issued in corresponding International Application No. PCT/US2012/052544, filed Aug. 27, 2012, 9 pages.

* cited by examiner

| QUESTION | ANSWER (CHOOSE ONE FOR EACH QUESTION) |
|---|---|
| 1. I COULD FEEL MY HEART BEAT FASTER | 1. (-0- NOT AT ALL) (-1- A LITTLE) (-2- A GREAT DEAL) (-3- EXTREMELY) |
| 2. I COULD NOT BREATHE WHEN I LAID DOWN | 2. (-0- NOT AT ALL) (-1- A LITTLE) (-2- A GREAT DEAL) (-3- EXTREMELY) |
| 3. I FELT PAIN IN MY CHEST | 3. (-0- NOT AT ALL) (-1- A LITTLE) (-2- A GREAT DEAL) (-3- EXTREMELY) |
| 4. I HAD AN UPSET STOMACH | 4. (-0- NOT AT ALL) (-1- A LITTLE) (-2- A GREAT DEAL) (-3- EXTREMELY) |
| 5. I HAD A COUGH | 5. (-0- NOT AT ALL) (-1- A LITTLE) (-2- A GREAT DEAL) (-3- EXTREMELY) |
| 6. I WAS TIRED | 6. (-0- NOT AT ALL) (-1- A LITTLE) (-2- A GREAT DEAL) (-3- EXTREMELY) |
| 7. I COULD NOT CATCH MY BREATH | 7. (-0- NOT AT ALL) (-1- A LITTLE) (-2- A GREAT DEAL) (-3- EXTREMELY) |
| 8. MY FEET WERE SWOLLEN | 8. (-0- NOT AT ALL) (-1- A LITTLE) (-2- A GREAT DEAL) (-3- EXTREMELY) |
| 9. I WOKE UP AT NIGHT BECAUSE I COULD NOT BREATHE | 9. (-0- NOT AT ALL) (-1- A LITTLE) (-2- A GREAT DEAL) (-3- EXTREMELY) |
| 10. MY SHOES WERE TIGHTER THAN USUAL | 10. (-0- NOT AT ALL) (-1- A LITTLE) (-2- A GREAT DEAL) (-3- EXTREMELY) |
| 11. I GAINED 3 OR MORE POUNDS IN THE PAST WEEK | 11. (-0- NOT AT ALL) (-1- A LITTLE) (-2- A GREAT DEAL) (-3- EXTREMELY) |
| 12. I COULD NOT DO MY USUAL DAILY ACTIVITIES BECAUSE I WAS SHORT OF BREATH | 12. (-0- NOT AT ALL) (-1- A LITTLE) (-2- A GREAT DEAL) (-3- EXTREMELY) |

Figure 2:
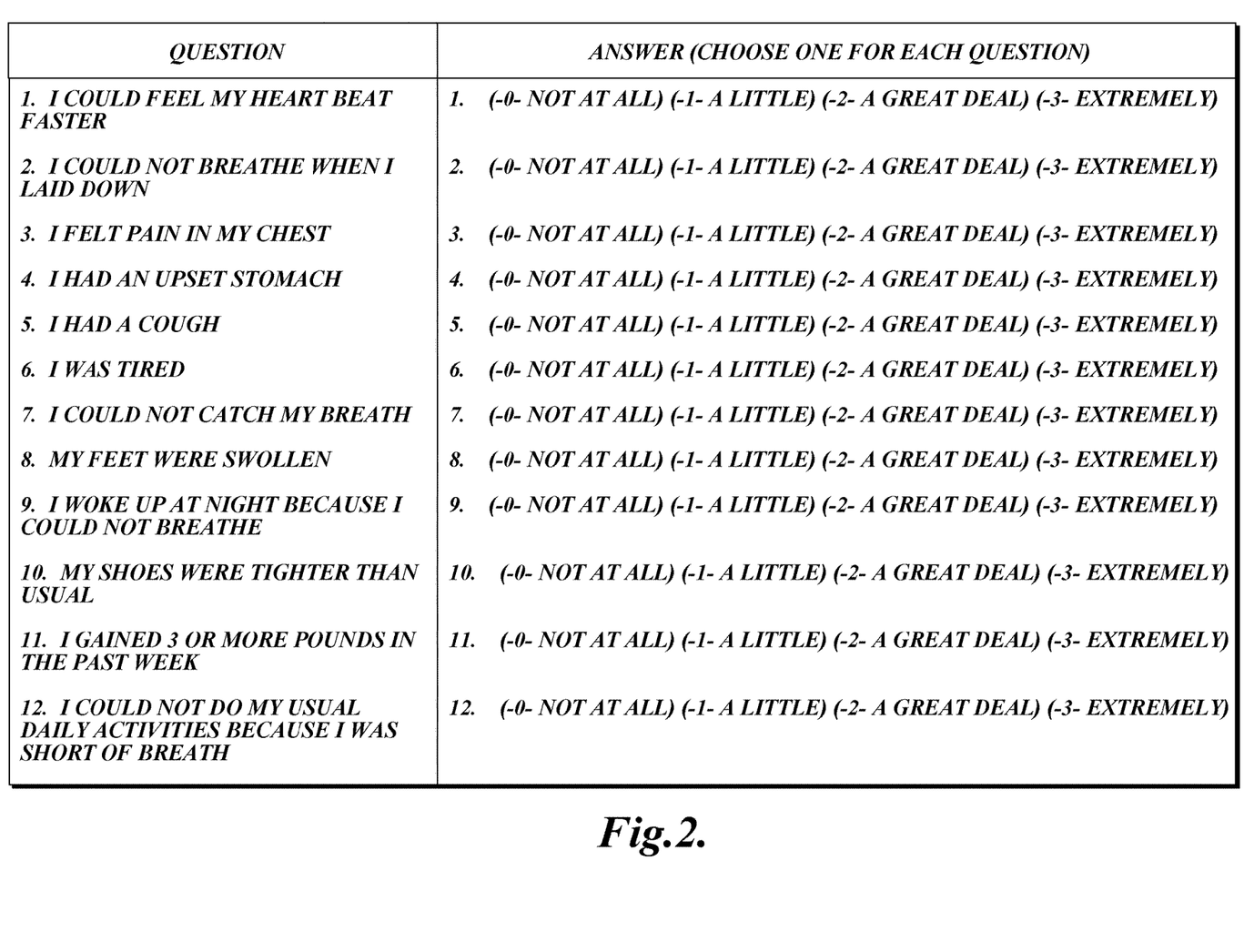

*Fig.2.*

| | a1 | a2 | a3 | a4 | a5 | a6 | a7 | a8 | a9 | a10 | a11 | a12 |
|---|---|---|---|---|---|---|---|---|---|---|---|---|
| Linear Regression | 0.61 | 0.79 | 0.41 | 0.28 | 0.3 | 0.78 | 0.44 | 0.88 | 0.29 | 0.9 | 0.42 | 0.84 |
| Simple Linear Regression | 0.5 | 0.75 | 0.34 | 0 | 0.2 | 0.85 | 0.32 | 0.9 | 0.24 | 0.92 | 0.4 | 0.85 |
| Pace Regression | 0.62 | 0.79 | 0.42 | 0.3 | 0.32 | 0.82 | 0.52 | 0.88 | 0.29 | 0.9 | 0.42 | 0.85 |
| Isotonic Regression | 0.53 | 0.76 | 0.23 | 0.12 | 0.18 | 0.86 | 0.38 | 0.89 | 0.1 | 0.92 | 0.29 | 0.85 |

Figure 3:
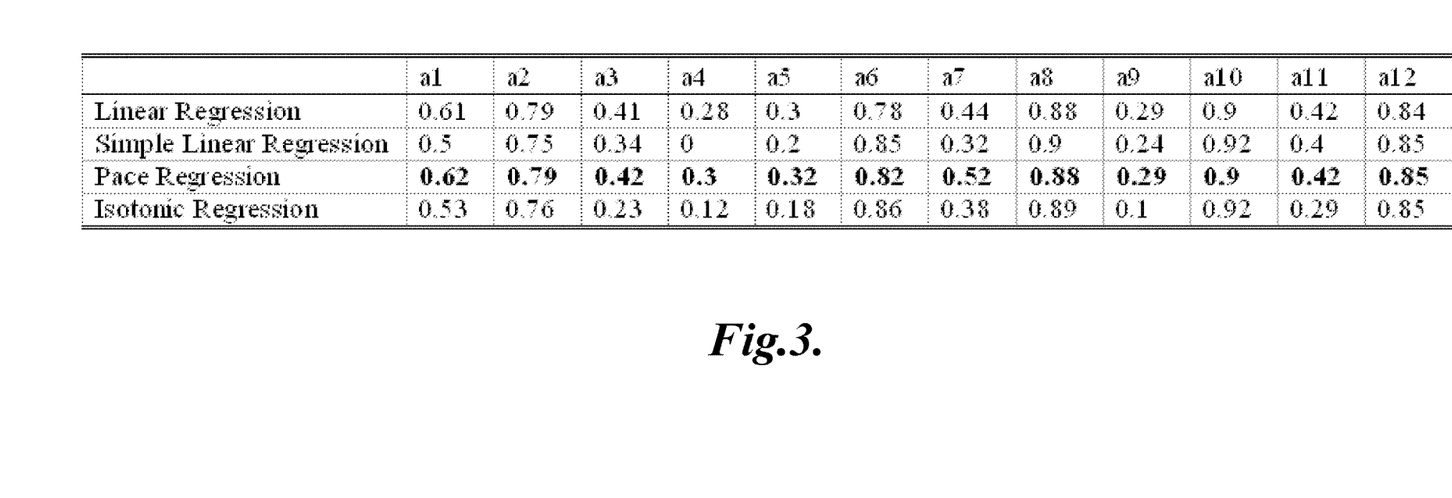

*Fig.3.*

Fig.4.

|  | Weight | Systolic | Diastolic | Heart Rate |
|---|---|---|---|---|
| C4.5 | 0 | 0 | 0.17 | 0.16 |
| Random Tree | 0.05 | 0 | 0.11 | 0.19 |
| Naive Bayes | 0.7 | 0.71 | 0.89 | 0.91 |
| Bayesian Network | 0.65 | 0.71 | 0.78 | 0.78 |
| VFI | 0.65 | 0.71 | 0.67 | 0.78 |
| Nnge | 0.05 | 0 | 0.11 | 0.28 |
| PART | 0.08 | 0 | 0.28 | 0.25 |
| DTNB | 0.03 | 0 | 0.44 | 0.13 |
| Decision Table | 0 | 0 | 0.22 | 0.06 |
| Rotation Forest | 0.05 | 0 | 0.17 | 0.03 |

Figure 5:
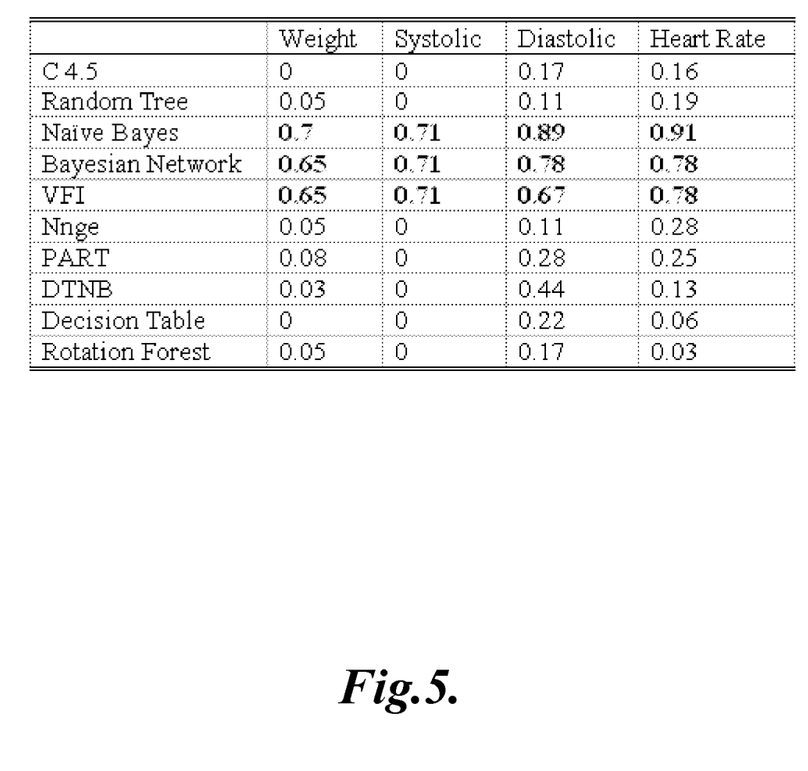

*Fig.5.*

|  |  | P1 | P2 | P3 | P4 | P5 | P6 | P7 | P8 | P9 | P10 | P11 | P12 | P13 | P14 | P15 | P16 | Group |
|---|---|---|---|---|---|---|---|---|---|---|---|---|---|---|---|---|---|---|
| weight | Naive Bayes | 0 | 0 | 0 | 0 | 0 | .33 | 0 | 0 | 0 | 0 | 0 | 1 | 0 | 0 | 0 | 0 | .7 |
|  | Bayes Net | 0 | 0 | 0 | 0 | 0 | .33 | 0 | 0 | 0 | 0 | 0 | 0 | 0 | .65 | 0 | 0 | .65 |
|  | VFI | 0 | 0 | 1 | 0 | 0 | .33 | 0 | 0 | 0 | 0 | 0 | 1 | 0 | .88 | 0 | 0 | .65 |
| systolic | Naive Bayes | 0 | .33 | 0 | 0 | 0 | 0 | 0 | .33 | 0 | 0 | 0 | 0 | 0 | .82 | 0 | 0 | .71 |
|  | Bayes Net | 0 | 0 | 0 | 0 | 0 | 0 | 0 | 0 | 0 | 0 | 0 | 0 | 0 | 0 | 0 | 0 | .71 |
|  | VFI | 0 | .33 | 0 | 0 | 0 | 0 | 0 | 0 | 0 | 0 | 0 | 0 | 0 | 0 | 0 | 0 | .71 |
| diastolic | Naive Bayes | 0 | .85 | 0 | 0 | 0 | 0 | 0 | 0 | 0 | 0 | 0 | 0 | 0 | 0 | 0 | 0 | .89 |
|  | Bayes Net | 0 | .39 | 0 | 0 | 0 | 0 | 0 | 0 | 0 | 0 | 0 | 0 | 0 | 0 | 0 | 0 | .78 |
|  | VFI | 0 | .62 | 0 | 0 | 0 | 0 | 0 | 0 | 0 | 0 | 0 | 0 | 0 | 0 | 0 | 0 | .67 |
| heart rate | Naive Bayes | 0 | .54 | 0 | 0 | 0 | 0 | 0 | 0 | 0 | 0 | 0 | 0 | 0 | 0 | 0 | .92 | .91 |
|  | Bayes Net | 0 | .31 | 0 | 0 | 0 | 0 | 0 | 0 | 0 | 0 | 0 | 0 | 0 | 0 | 0 | .75 | .78 |
|  | VFI | 0 | .69 | 0 | 0 | 0 | 0 | 0 | 0 | 0 | 0 | 0 | 0 | 0 | 0 | 0 | .67 | .78 |

Figure 6:
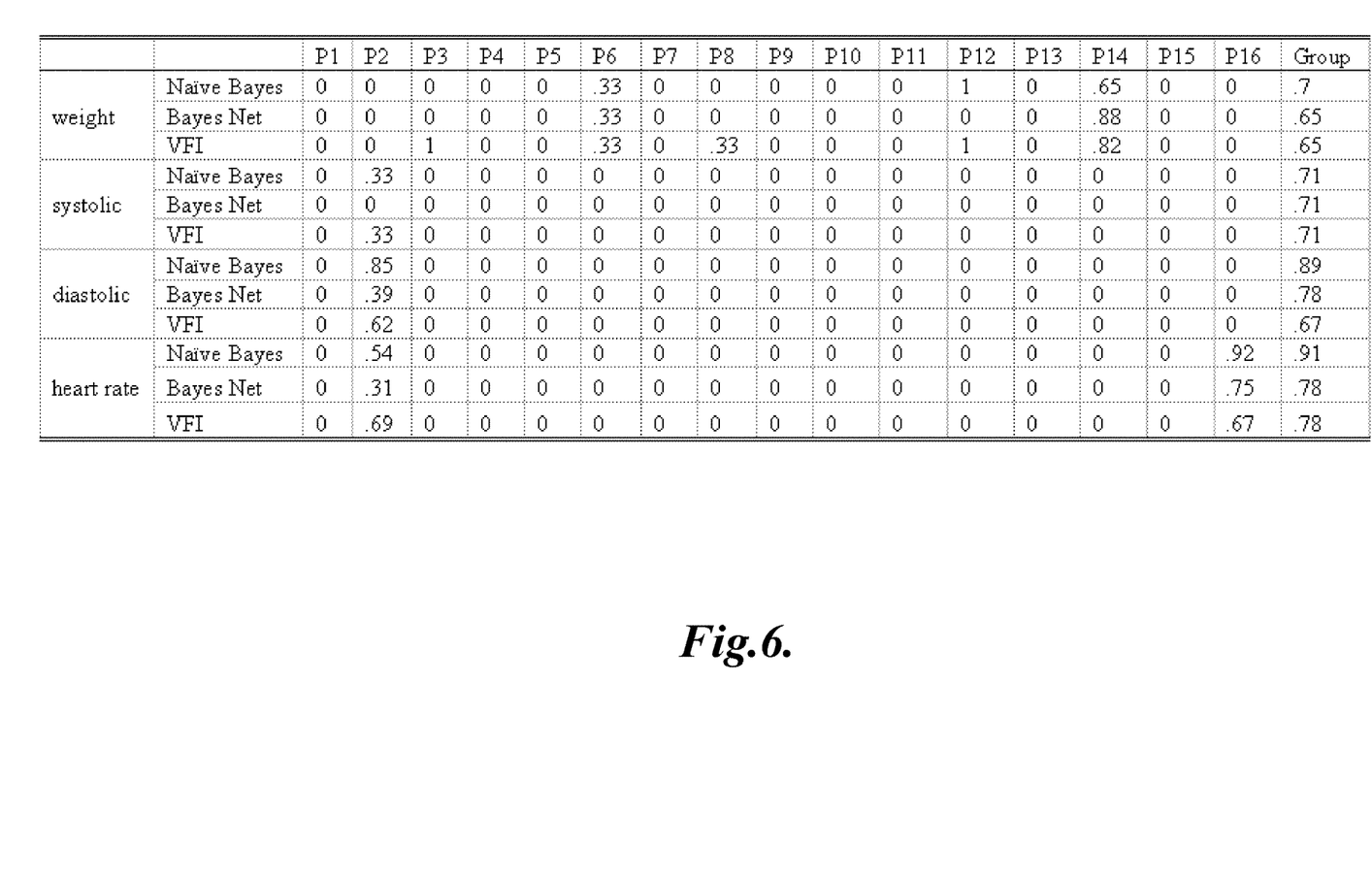

*Fig.6.*

SYSTEMS AND METHODS FOR MISSING DATA IMPUTATION

STATEMENT OF GOVERNMENT LICENSE RIGHTS

This invention was made with Government support under Grant No. LM007356, awarded by the National Institutes of Health. The Government has certain rights in this invention.

Congestive heart failure (CHF) is a leading cause of death in the United States with approximately 670,000 individuals diagnosed every year. The sequelae of CHF are well known, with frequent decompensation of the chronic state resulting in recurrent hospitalizations. Experts believe that constant monitoring of patients with CHF is important to the health of such patients.

Remote patient monitoring is a promising solution for an expanding population of CHF patients who are unable to access clinics due to insufficient resources, inconvenient location, or advanced infirmity. Medical care facilitated by remote technology has the potential to enable early detection of key clinical symptoms indicative of CHF-related decompensation. Such remote technologies can also enable health professionals to offer surveillance, advice, and continuity of care to trigger early implementation of strategies that enhance adherence behaviors.

The WANDA (Weight and Activity) project is one example of a wireless health project that leverages sensor technologies and remote communication to monitor the health status of patients with CHF. WANDA monitors health-related measurements and other information deemed relevant to CHF assessment, including weight, blood pressure, heart rate, activity, and daily somatic awareness scale questionnaires. Detailed descriptions of the WANDA system and its use for monitoring CHF patients can be found in Suh, M. et al., "WANDA B.: Weight and activity with blood pressure monitoring system for heart failure patients," in 2010 IEEE International Symposium on A World of Wireless, Mobile and Multimedia Networks (WoWMoM), 2010, pp. 1-6; Suh, M. et al., "An automated vital sign monitoring system for congestive heart failure patients," Proceedings of the 1st ACM International Health Informatics Symposium, 2010; and Suh, M. et al., "A remote patient monitoring system for congestive heart failure," Journal of Medical Systems, 2011, all of which are incorporated herein by reference in their entirety for all purposes.

It is desired for a remote monitoring system such as WANDA to collect and store all monitored vital signs. Any unhealthy changes in a patient's vital signs should be addressed promptly in order to prevent further degradation of a patient's health. Unfortunately, the first randomized trial of WANDA experienced a considerable amount of missing data. Only 33% of the somatic questionnaires were completed, and 55.7% of data had missing values for weight, blood pressure, and heart rate. Moreover, 22.2% of patients experienced system misuse and requested help to accustom themselves to WANDA's technologies. Missing data was further caused by system nonuse and service disorder (such as a network failure, resulting in as much as 6.3% of all of the missing data).

Notably, other studies have experienced similar data loss. Missing data is especially common in randomized controlled trials. Wood's study showed that 89% of 71 trials published in 2001 in well-known journals (the British Medical Journal, the Journal of the American Medical Association, the Lancet, and the New England Journal of Medicine) reported having partly missing outcome values. Many studies applied last observation carried forward, worst case imputation, and complete case analysis techniques. However, such techniques may lead to biased results.

To date, there has been no study on missing data imputation in CHF randomized trials. One objective of embodiments of the present disclosure is to enhance the accuracy of CHF missing data imputation using data mining techniques. Data imputation may allow a patient monitoring system to detect an unhealthy change in patient vital signs even when portions of that data are not collected by the system. Embodiments of the present disclosure exploit the projection adjustment by contribution estimation (PACE) regression method for predicting and imputing non-binomial data such questionnaire responses. Bayesian methods and voting feature interval (VFI) are used to impute binomial data. Results of these methods may be compared using accuracy and correlation efficient values for non-binomial cases, and recall values for binomial cases. Previous methods may be compared with several other popular data mining methods. The experimental results show that PACE regression, Bayesian methods, and voting feature interval are superior to other methods for CHF patient data imputation.

Figure 1:
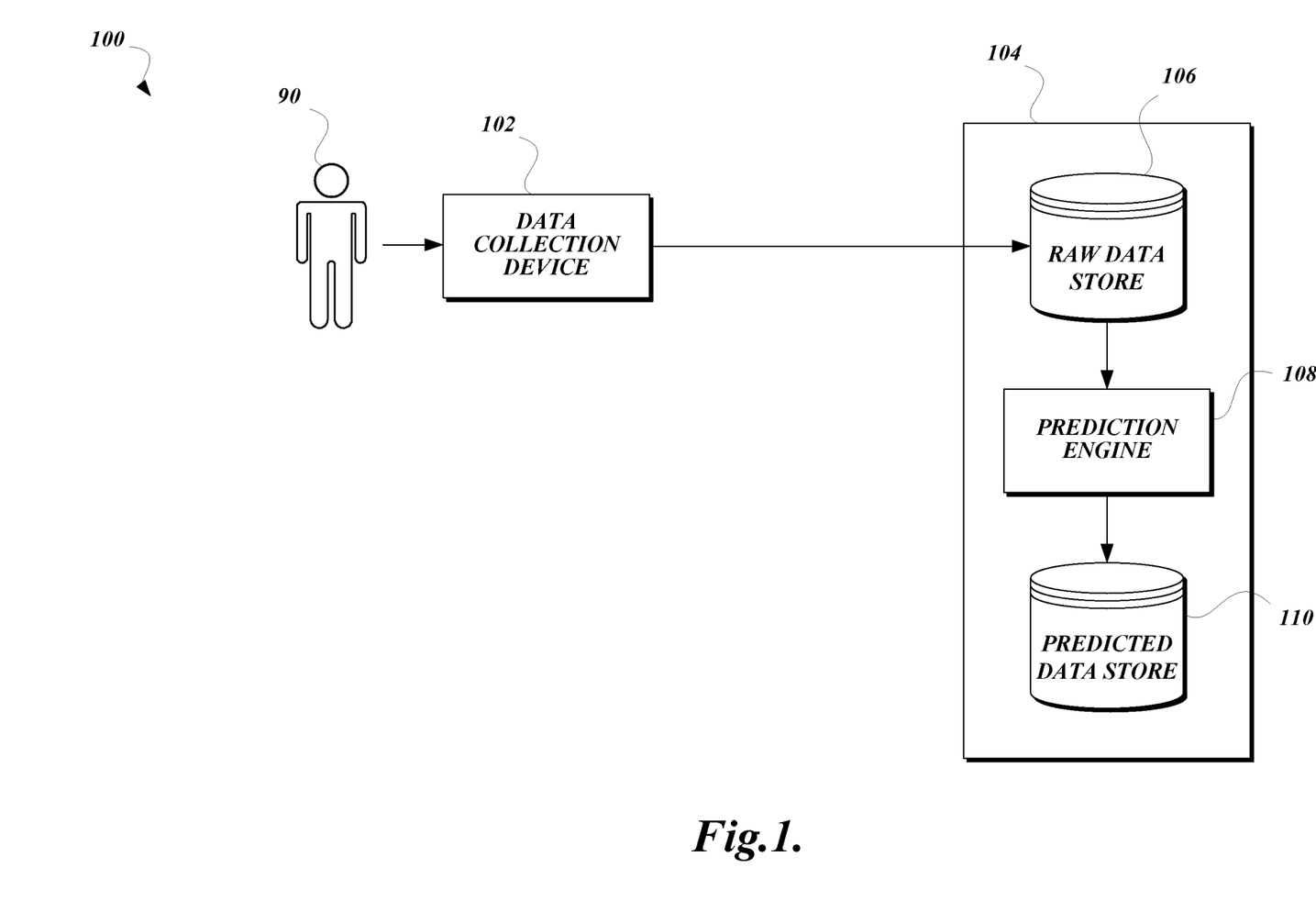

FIG. 1 illustrates a block diagram of a system 100 for collecting and imputing patient health data. Patient data is collected from a patient 90 by at least one data collection device 102. As described above with respect to WANDA, the at least one data collection device may include a scale, a heart rate monitor, a blood pressure monitor, a motion-sensing activity monitor, and/or a computing device configured to collect questionnaire answers. In one embodiment, the data collection device 102 may be a separate device that collects data values from such devices at the location of the patient 90.

The data collection device 102 transmits the data to a patient data computing device 104, where the patient data is stored in a raw data store 106. In one embodiment, the data collection device 102 transmits the data to the patient data computing device 104 over a network such as a public switched telephone network; a wide area network; a local area network; the Internet; a wireless network such as 3G, 4G, LTE, GSM, Bluetooth, WiFi, WiMax; and/or via any other suitable networking technology. In another embodiment, the data collection device 102 may be transported to the location of the patient data computing device 104, and may transmit the data to the patient data computing device 104 via a direct data connection between the devices, such as a USB connection, a Firewire connection, and/or the like.

A prediction engine 108 may then impute missing patient data values as discussed further below, and may store the imputed patient data values in a predicted data store 110. In some embodiments, the prediction engine 108 may search for missing values, and then perform the calculations described below to predict the missing values. If the predicted values are beyond threshold limits, such as a threshold limit specified by a caregiver, the patient data computing device 104 may generate an alert to be presented to the caregiver. The alert may include one or more predicted or measured values, which may then prompt the caregiver to check the status of the patient or to ask the patient to verify the predicted values. In cases where the predicted values do not match the actual status of the patient, the prediction engine 108 may use the actual status as training data for a subsequent prediction.

In some embodiments, the prediction engine 108 may include one or more computer-executable components stored on a computer-readable medium that, if executed by a processor of a computing device, cause the computing device to perform the actions described below. In some embodiments, the prediction engine 108 may include one or more computing devices specially configured to perform the described actions.

In some embodiments, the raw data store 106 and the predicted data store 110 may be databases managed by a conventional relational database management system (RDBMS). One of ordinary skill in the art will recognize that the raw data store 106 and the predicted data store 110 may be separate databases, or may be stored in a single database. In other embodiments, the raw data store 106 and/or the predicted data store 110 may use any other suitable storage method, such as a structured query language (SQL) file, a spreadsheet, a text document, and/or the like.

In some embodiments, the patient data computing device 104 may include at least one processor, an interface for coupling the computing device to the data collection device 102, and a nontransitory computer-readable medium. The computer-readable medium may have computer-executable instructions stored thereon that, in response to execution by the processor, cause the patient data computing device 104 to perform the calculations described further below. One example of a suitable computing device is a personal computer specifically programmed to perform the actions described herein. This example should not be taken as limiting, as any suitable computing device, such as a laptop computer, a smartphone, a tablet computer, a cloud computing platform, an embedded device, and/or the like, may be used in various embodiments of the present disclosure. One of ordinary skill in the art will recognize that the components illustrated as part of the patient data computing device 104 may be combined into a single component, or may each be split apart into multiple components. Further, the patient data computing device 104 may be a single computing device that stores and/or executes each of the illustrated components, or may include multiple computing devices communicatively coupled to each other that each store and/or execute part or all of the illustrated components.

Non-Binomial Case Imputation

In one embodiment, WANDA may employ the Heart Failure Somatic Awareness Scale (HFSAS) which is a 12-item Likert-type scale to measure awareness of signs and symptoms specific to CHF. A 4-point Likert-type scale is used to ascertain how much a patient is bothered by a symptom (0: not at all, 1: a little, 2: a great deal, 3: extremely). FIG. 2 illustrates one example of an embodiment of an HFSAS questionnaire.

In order to predict missing answers to such a questionnaire, embodiments of the present disclosure may use the projection adjustment by contribution estimation regression algorithm (PACE) (rounding any non-integer value returned by PACE). This method is based on maximum likelihood estimation (MLE) and an empirical Bayes framework to minimize the Kullback-Leibler (KL) distance between the original and the estimation function.

First, the PACE algorithm transforms parameters using MLE's asymptotic normality property to convert the original parameters. The algorithm utilizes the empirical Bayes estimator in (1):

$$\theta^{LB} = \frac{\int \theta f(x_i \mid \theta) dG_k(\theta)}{\int f(x_i \mid \theta) dG_k(\theta)} \quad (1)$$

where $\check{\theta}(x)$ is the estimator, $f(x_i|\theta_i)$ is a probability density function (PDF) and $G_k$ is a consistent estimator of G which is the mixing distribution of the mixture $f_G(x) = \int f(x|\theta) dG$. Using (2), the developed algorithm minimizes the KL distance between f and $\check{f}$ in (2):

$$\Delta_{KL}(f, \check{f}) = E_f \log\left(\frac{f}{\check{f}}\right) = \int \log\left(\frac{f}{\check{f}}\right) f dx \quad (2)$$

This method may show better results in high dimensional data spaces, and was applied to complete cases that have all 12 answered questions to evaluate the accuracy.

Binomial Case Imputation

A binomial approach may be used to predict alarms normally triggered by abnormal data values (e.g., drastic weight changes, unhealthy blood pressure, etc.) given missing data. For example, the system may be configured to trigger an alarm if a patient has an extreme change in weight—even when the extreme weight value is missing from the data collected by WANDA. Embodiments of the present disclosure may use naïve Bayes, a Bayesian network, and VFI to detect such changes in order to alert caregivers.

Naïve Bayes and Bayesian network classifiers are algorithms that approach the classification problem using the conditional probabilities of the features. A Bayesian network is a directed acyclic graph (DAG) over a set of variables X, where the outgoing edges of a variable $x_i$ specifies all variables that depend on $x_i$. The probability of an outcome is determined as:

$$P(X) = \Pi_{x \in X} p(x|\text{par}(x)) \quad (3)$$

where $X = \{x_1, x_2, \ldots, x_k\}$ is a set of variables, and par(x) is the set of parents of x in a Bayesian network. The probability of the instance belonging to a single class may be calculated by using the prior probabilities of classes and the feature values for an instance. Naive Bayesian method assumes that features are independent and there are no hidden or latent attributes in the prediction process. As such, the experimental results for naïve Bayes and Bayesian network can be slightly different as $$p(\text{class}) = \frac{1 + N(\text{class})}{N(\text{class}) + N(\text{instances})}$$

for naïve Bayes and $$p(\text{class}) = \frac{\frac{1}{2} + N(\text{class})}{N(\text{class}) \times \frac{1}{2} + N(\text{instances})}$$

for Bayesian network where N(x) is the number of sets or instances.

VFI is a categorical classification algorithm and considers each feature independently as Bayes methods. The classification of a new instance may be based on a vote among the classifications built by the value of each feature. While training, the VFI algorithm constructs intervals for each feature. For the classification, a single value and the votes of each class in that interval are calculated for each interval. For each class c, feature f gives a vote value:

$$\text{feature\_vote}[f, c] = \frac{\text{interval\_class\_count}[f, i, c]}{\text{class\_count}[c]} \quad (4)$$

where interval_class_count[f,i,c] is the number of instances of class c which is a member of interval i of feature f. The class with the highest total vote is predicted to be the class of the test instance.

In the Bayes methods, each feature participates in the classification by assigning probability for each class and the final probability of a class is the product of each probability measured on each feature. In VFI, each feature distributes its vote among classes and the final vote of a class is the sum of each vote given the features.

Subjects and Datasets

The WANDA system was used for health data collection on 26 different subjects. The population of the participants was approximately 68% male; 40% White, 13% Black, 32% Latino, and 15% Asian/Pacific Islander; with a mean age of approximately 68.7±12.1. Study participants were all provided with Bluetooth weight scales, blood pressure monitors, land line gateways, and personal activity monitor devices. Each captured data instance for the study comprises 37 different attributes including, but not limited to: timestamps; weight; diastolic/systolic blood pressure; heart rate; metabolic equivalents (METs); calorie expenditure; and numeric responses to twelve somatic awareness questions. Each data instance was gathered from each subject once a day. One thousand and ninety instances were gathered.

The study used the missing at random (MAR) hypothesis. MAR assumes that missing data is dependent on observed data. Hence, missing data can be predicted by resident data. All 1090 instances of data are complete (i.e., contain all 37 data values). Instances were divided into to two groups: training and testing. Values from the testing set predicted by the data imputation techniques were compared to their actual values to evaluate the effectiveness of each system.

EXAMPLE RESULTS

For non-binomial data, PACE, linear, simple linear and isotonic regression methods were applied. FIG. 3 is a table showing the correlation coefficient values of each method. Correlation coefficient is a measure of least square fitting to the original data. For a given N data points (X,Y), the correlation coefficient $\rho_{X,Y}$ is given as equation (5) where COV(X,Y) is a covariance between X and Y and $\sigma_X$, $\sigma_Y$ are standard deviation values of X and Y. The experimental results show that PACE regression method works better on average than other given regression methods.

$$\rho_{X,Y} = \frac{\text{COV}(X, Y)}{\sigma_X \times \sigma_Y} \quad (5)$$

Figure 4:
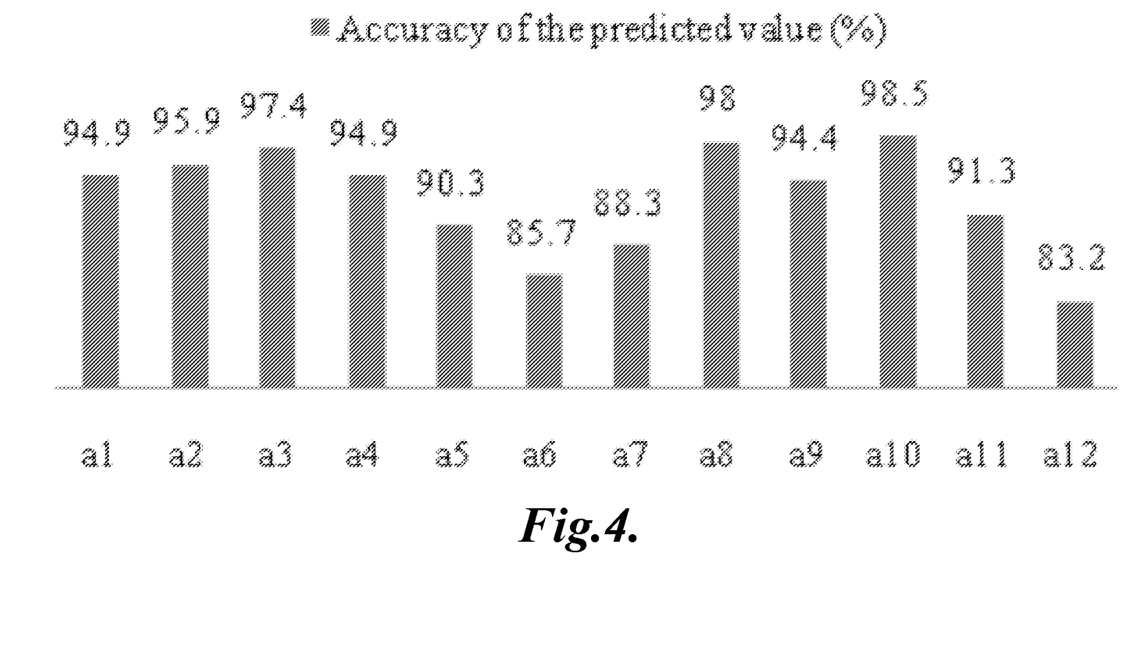

After calculating the coefficient and constant variables, the developed algorithm determines missing values using PACE regression (rounding any non-integer value returned by PACE). The accuracies of the obtained values range between 83.2% and 98.5%, as shown in FIG. 4.

The binomial case predicts a potential abnormal vital sign when missing data exist within WANDA's database. C4.5, random tree, naïve Bayes, Bayesian network, VFI, nearest neighbor, PART, DTNB, decision table, and rotation table algorithms were applied and their recall values were compared. For each method, ten-fold cross validation was applied. In ten-fold validation, the original sample is randomly partitioned into ten subsets and a single subset is held as a testing model, with the remaining nine subsets are used as training data. This cross-validation process is then repeated ten times, using a new subset as a testing model for each repetition. Recall values are given as:

$$\text{recall} = \frac{Tp}{Tp + Fn} \quad (6)$$

where $T_p$ is true positive and $F_n$ is false negative. FIG. 5 is a table that illustrates the experimental result, and shows that naive Bayes, Bayesian network, and VFI have recall values of up to 0.7 for weight, 0.714 for systolic blood pressure, 0.889 for diastolic blood pressure and 0.906 for heart rate values.

Classifiers were trained in two ways. First, unique classifiers were created for each individual where only data collected from an individual was used to predict values from the same individual. Second, a grouped classifier was created using data from the entire population. Both the individual and grouped classifiers were compared using ten-fold validation to test data from 16 patients. The recall values of weight, blood pressure, and heart rate are improved when training on the entire group's data as compared with training each individual's data separately. FIG. 6 is a table that illustrates the recall values. For questionnaire data, the accuracies of results were also better when training on all patients' data. When training individually, 75% of patients' data showed 0% accuracy. This is because the entire group has bigger number of data and many individual share similarities in monitored attributes, such as age, symptoms of CHF, etc.

The accuracy of the CHF missing data was enhanced using the PACE regression method for predicting and imputing non-binomial data; and Bayesian methods and voting feature interval for binomial data. The experimental results show that PACE regression works better than linear regression, simple linear regression, and isotonic regression methods with accuracy values of more than 83.2%. The experiment comparing Bayes and VFI methods with other algorithms proves that Bayes and VFI algorithms work better (FIG. 5) with recall values of up to 0.7 for weight, 0.714 for systolic blood pressure, 0.889 for diastolic blood pressure and 0.906 for heart rate values. This study also showed that increased accuracy is obtained by training on a large population as opposed to training the classifiers for each individual independently.

While a preferred embodiment of the invention has been illustrated and described, it will be appreciated that various changes can be made therein without departing from the spirit and scope of the invention.

The invention claimed is:

1. A system configured to impute missing patient data for health care monitoring of a patient with a congestive heart failure condition, the system comprising:
   a raw data store configured to store raw patient data received from the patient, the raw patient data including questionnaire data provided manually by the patient and sensor data provided by one or more sensor devices;

a prediction engine configured to automatically impute missing binomial data values and missing non-binomial data values based on the raw patient data stored in the raw data store, wherein the prediction engine is configured to impute values of the questionnaire data and the sensor data that are missing in the raw data store using a projection adjustment by contribution estimation (PACE) regression, wherein the prediction engine includes a classifier that is configured to classify a predicted value of the imputed values from the PACE regression as being beyond a threshold limit, wherein the classifier is trained using patient data from a plurality of patients other than the patient;
a predicted data store configured to store imputed patient data generated by the prediction engine; and
an alert module configured to generate an alert in response to the predicted value being classified as beyond the threshold limit, wherein the alert is configured to prompt a caregiver to determine whether the current status of the patient with the congestive heart failure condition is consistent with the predicted value.

2. The system of claim 1, wherein the raw patient data includes data relevant to congestive heart failure assessment comprising one or more of weight data, blood pressure data, heart rate data, activity data, and somatic awareness scale questionnaire data.

3. The system of claim 1, wherein using the projection adjustment by contribution estimation (PACE) regression includes transforming original parameters using an asymptotic normality property of maximum likelihood estimation (MLE) to convert the original parameters.

4. The system of claim 3, wherein using the projection adjustment by contribution estimation (PACE) regression further includes using an empirical Bayes estimator, wherein the empirical Bayes estimator is defined as $$\theta_i^{EB} = \frac{\left(\int \theta f(x_i \mid \theta) dG_k(\theta)\right)}{\int f(x_i \mid \theta) dG_k(\theta)}$$

wherein $\theta(x)$ is the estimator, $f(x_i \mid \theta_i)$ is a probability density function (PDF), and $G_k$ is a consistent estimator of G which is the mixing distribution of the mixture $f_G(x) \int f(x \mid \theta) dG$.

5. The system of claim 4, wherein imputing the missing questionnaire data values further comprises minimizing a Kullback-Leibler (KO) distance between f and $\tilde{f}$ using a function defined as $$\Delta_{KL}(\tilde{f}, f) = E_f \log\left(\frac{f}{\tilde{f}}\right) = \int f \log\left(\frac{f}{\tilde{f}}\right) f \, dx.$$

6. The system of claim 1, wherein the prediction engine is configured to impute the missing binomial data values of the patient data using naïve Bayes calculations, Bayesian network calculations, or voting feature interval (VFI) calculations to predict a potential abnormal patient data value.

7. The system of claim 6, wherein the Bayesian network calculations include generating a directed acyclic graph (DAG) over a set of variables X, wherein outgoing edges of a variable xi specifies all variables that depend on xi, and wherein a probability of an outcome is determined as $P(X) = \Pi_{x \in x} P(x \mid \text{par}(x))$ wherein $X = \{x\_1, x\_2, \ldots, x_k\}$ is a set of variables, and par(x) is the set of parents of x in a Bayesian network.

8. The system of claim 6, wherein experimental results for the naïve Bayes calculations are determined as $$p(\text{class}) = \frac{1 + N(\text{class})}{N(\text{class}) + N(\text{instances})}$$

and wherein experimental results for the Bayesian network calculations are determined as $$p(\text{class}) = \frac{\frac{1}{2} + N(\text{class})}{N(\text{class}) \times \frac{1}{2} + N(\text{instances})}$$

wherein N(x) is a number of sets or instances.

9. The system of claim 6, wherein the voting feature interval (VFI) calculations include:
constructing intervals for each feature;
calculating for each interval a single value and votes of each class in the interval; and
calculating a vote value for each class c and feature f via the calculation $$[f, c] = \frac{\text{interval\_class}_{count}[f, i, c]}{\text{class\_count}[c]}$$

wherein interval_class_count[f,i,c] is a number of instances of class c, which is a member of interval i of feature f.

10. The system of claim 1, wherein the questionnaire data values being imputed include somatic awareness scale answers that measure awareness of signs and symptoms associated with congestive heart failure.

11. The system of claim 1, wherein the prediction engine is configured to perform rounding of non-integer values returned by the projection adjustment by contribution estimation (PACE) regression to obtain the missing questionnaire data values.

12. The system of claim 1, wherein the alert may include one or more predicted and measured values for the patient with the congestive heart failure condition that are presented to the caregiver for performing the status check.

13. A computer-implemented method of imputing missing data for monitoring health of a patient with a congestive heart failure condition, the method comprising:
receiving raw patient data from the patient, the raw patient data including questionnaire data provided manually by the patient and sensor data provided by one or more sensor devices;
imputing, by a computing device, one or more missing binomial patient data values and one or more missing non-binomial patient data values using at least one data mining technique; and
predicting an alert condition based on at least the imputed missing patient data values, the alert condition being generated in response to a predicted value of the imputed missing patient data values being classified as beyond a threshold limit, wherein the alert is configured to prompt a caregiver to determine whether the current status of the patient with the congestive heart failure condition is consistent with the predicted value, and wherein predicting the alert condition includes predicting cardiac decompensation associated with congestive heart failure, and wherein receiving raw patient data includes receiving one or more of weight data, blood pressure data, heart rate data, activity data, and somatic awareness scale questionnaire data, and wherein predicting further includes imputing values of the questionnaire data and the sensor data that are missing in the raw patient data using a projection adjustment by contribution estimation (PACE) regression, and wherein predicting further includes classifying the predicted value from the PACE regression as being beyond the threshold limit, wherein the classifier is trained using patient data from a plurality of patients other than the patient.

14. The method of claim 13, wherein using the projection adjustment by contribution estimation (PACE) regression includes transforming original parameters using an asymptotic normality property of maximum likelihood estimation (MLE) to convert the original parameters.

15. The method of claim 14, wherein using the projection adjustment by contribution estimation (PACE) regression further includes using an empirical Bayes estimator, wherein the empirical Bayes estimator is defined as $$\theta_i^{EB} = \frac{\left(\int \theta f(x_i \mid \theta) dG_k(\theta)\right)}{\int f(x_i \mid \theta) dG_k(\theta)}$$

wherein $\check{\theta}(x)$ is the estimator, $f(x_i|\theta_i)$ is a probability density function (PDF), and $G_k$ is a consistent estimator of G which is the mixing distribution of the mixture $f_G(x) = \int f(x|\theta)dG$.

16. The method of claim 15, further comprising minimizing a Kullback-Leibler (KL) distance between f and $\tilde{f}$ using a function defined as $$\Delta_{KL}(f, \tilde{f}) = E_f \log\left(\frac{f}{\tilde{f}}\right) = \int \log\left(\frac{f}{\tilde{f}}\right) f \, dx.$$

17. The method of claim 13, wherein imputing includes predicting the missing binomial patient data values using one or more of naïve Bayes calculations, Bayesian network calculations, and voting feature interval (VFI) calculations.

18. The method of claim 17, wherein the Bayesian network calculations include generating a directed acyclic graph (DAG) over a set of variables X, wherein outgoing edges of a variable xi specifies all variables that depend on xi, and wherein a probability of an outcome is determined as $$P(X) = \Pi_{x \in X} P(x|par(x))$$

wherein X={xi, x2, . . . , xk} is a set of variables, and par(x) is the set of parents of x in a Bayesian network.

19. The method of claim 17, wherein experimental results for the naïve Bayes calculations are determined as $$p(\text{class}) = \frac{1 + N(\text{class})}{N(\text{class}) + N(\text{instances})}$$

and wherein experimental results for the Bayesian network calculations are determined as $$p(\text{class}) = \frac{\frac{1}{2} + N(\text{class})}{N(\text{class}) \times \frac{1}{2} + N(\text{instances})}$$

wherein N(x) is a number of sets or instances.

20. The method of claim 17, wherein the voting feature interval (VFI) calculations include:
constructing intervals for each feature;
calculating for each interval a single value and votes of each class in the interval; and
calculating a vote value for each class c and feature f via the calculation $$f[f, c] = \frac{\text{interval\_class}_{count}[f, i, c]}{\text{class\_count}[c]}$$

wherein interval class count[f,i,c] is a number of instances of class c, which is a member of interval i of feature f.

21. The method of claim 13, wherein predicting the missing questionnaire data values includes rounding of non-integer values returned by the projection adjustment by contribution estimation (PACE) regression to obtain the missing questionnaire data values.

* * * * *